(12) United States Patent
Amato et al.

(10) Patent No.: US 10,190,800 B2
(45) Date of Patent: Jan. 29, 2019

(54) HEATABLE FLUID BAG

(71) Applicants: David John Amato, Auckland (NZ); Huiquan Zhang, NingBo (CN)

(72) Inventors: David John Amato, Auckland (NZ); Huiquan Zhang, NingBo (CN)

( * ) Notice: Subject to any disclaimer, the term of this patent is extended or adjusted under 35 U.S.C. 154(b) by 0 days.

(21) Appl. No.: 15/770,244

(22) PCT Filed: Nov. 18, 2015

(86) PCT No.: PCT/CN2015/094877
§ 371 (c)(1),
(2) Date: Apr. 23, 2018

(87) PCT Pub. No.: WO2017/079989
PCT Pub. Date: May 18, 2017

(65) Prior Publication Data
US 2018/0306465 A1 Oct. 25, 2018

(30) Foreign Application Priority Data
Nov. 13, 2015 (CN) .......................... 2015 1 0774117

(51) Int. Cl.
*A61F 7/08* (2006.01)
*A47J 27/00* (2006.01)
(Continued)

(52) U.S. Cl.
CPC ............ *F24H 9/2021* (2013.01); *A61F 7/007* (2013.01); *A61F 7/0085* (2013.01); *A61F 7/086* (2013.01); *F24H 1/202* (2013.01); *F24H 9/1827* (2013.01)

(58) Field of Classification Search
None
See application file for complete search history.

(56) References Cited

U.S. PATENT DOCUMENTS 6,480,257 B2 * 11/2002 Cassidy ................ A61M 5/365
165/46
6,788,885 B2 * 9/2004 Mitsunaga .............. A61M 5/44
392/470
(Continued)

FOREIGN PATENT DOCUMENTS

AU  2014-202058 B1  4/2015
CN     2813943 Y     9/2006
(Continued)

OTHER PUBLICATIONS

Aug. 5, 2016 Internation Search Report issued in International Patent Application No. PCT/CN2015/094877.

*Primary Examiner* — Thor Campbell
(74) *Attorney, Agent, or Firm* — Oliff PLC

(57) ABSTRACT

A heatable fluid bag, including a bag body, wherein a liquid inlet and power access port are formed in the bag body; the power access port is electrically connected with an electrical heating component installed in the bag body; the electrical heating component includes a metal ceramic heating sheet; the metal ceramic heating sheet is encapsulated in a metal protection shell composed of an upper and lower sheet; a connection base is connected to the upper sheet; a PVC protection shell is installed in the connection base; a power connector installation shell is installed in the PVC protection shell; a temperature control K301 switch, thermal fuse and power input socket are installed in the power connector installation shell; and a rotary upper cover is installed on the power input socket. The fluid bag is simple in structure, separates water and electricity, and is waterproof and insulating.

11 Claims, 5 Drawing Sheets

(51) Int. Cl.
*F24H 9/20* (2006.01)
*F24H 1/20* (2006.01)
*A61F 7/00* (2006.01)
*F24H 9/18* (2006.01)

(56) References Cited

U.S. PATENT DOCUMENTS

| | | | | |
|---|---|---|---|---|
| 6,882,797 | B2* | 4/2005 | Stewart | A61M 5/445 |
| | | | | 219/518 |
| 7,164,852 | B2* | 1/2007 | Cazzini | A61M 5/445 |
| | | | | 392/470 |
| 7,289,724 | B2* | 10/2007 | Furnrohr | A61M 1/0281 |
| | | | | 392/470 |
| 7,394,976 | B2* | 7/2008 | Entenman | A61F 7/0085 |
| | | | | 392/470 |
| 7,720,362 | B2* | 5/2010 | Arnold | A61F 7/0085 |
| | | | | 392/470 |
| 8,224,166 | B2* | 7/2012 | Theilacker-Beck | A61M 5/36 |
| | | | | 392/443 |
| 8,662,154 | B2* | 3/2014 | Smisson, III | A61M 1/0281 |
| | | | | 165/181 |
| 2012/0191164 | A1 | 7/2012 | Gander et al. | |

FOREIGN PATENT DOCUMENTS

| | | |
|---|---|---|
| CN | 200950663 Y | 9/2007 |
| CN | 201910932 U | 7/2011 |
| CN | 202759603 U | 2/2013 |
| CN | 204206489 U | 3/2015 |
| CN | 104566935 A | 4/2015 |
| EP | 2 925 085 A1 | 9/2015 |

* cited by examiner

HEATABLE FLUID BAG

TECHNICAL FIELD

The present invention relates to a heating appliance, particularly to an electric liquid (water) heater, and more particularly to a heatable fluid bag.

RELATED ART

At present, an electric hot water bag is a heating appliance commonly used in winter, which has the advantage of fast heating, is convenient to use, can be used for warming the hands, the chest, the abdomen, and other parts, and can also be used for local warming. The electric hot water bag is a device utilizing electricity to heat liquid in a bag. Common heating elements include an electric heating wire, an electric heating tube, and the like, and it is difficult to solve the problem of preventing electric leakage during heating. Because the liquid (mostly tap water) in the bag is easy to infiltrate into electrical components to cause short circuit or electric leakage, electric insulation has always been the focus of attention. However, in actual use, people find that an electric heating element is most likely to malfunction and seriously affect its service life, so finding alternative electric heating elements is the key to ensure the electrical appliance safety, to increase the heating efficiency, and to prolong the service life.

In recent years, a metal ceramic heating element has been widely applied to water heating. Because of the advantages of water proofing, insulation, electrical appliance safety, small size, high efficiency, and long life, applying the metal ceramic heating element to a liquid heating device (electric hot water bag) has a broad market, and the metal ceramic heating element is an upgraded product that will certainly be favored by people.

In the present specification, unless explicitly stated to the contrary, where documents, entries, or items of knowledge are referred to or discussed, such reference or discussion is not an admission that the documents, entries, or items of knowledge, or any combination thereof are common knowledge publicly available at a priority date, publicly known and partially known, or are known to attempt to solve any of the problems involved in the present specification.

SUMMARY

The present invention is directed to a heatable fluid device with an electric heating element made of metal ceramics, which is intended to solve the problems of electrical appliance safety such as short service life, low efficiency, large size, and poor waterproof insulation of an electric heating wire, an electric heating tube or other electric heating elements in an existing liquid heating device.

The first technical solution of the present invention is as follows.

A heatable fluid bag comprises a bag body 1, a liquid inlet 4 and a power access port 41 being formed in the bag body 1, an extractable liquid inlet plunger 3 being installed in the liquid inlet 4, and the power access port 41 being electrically connected with an electrical heating component installed in the bag body 1. The heatable fluid bag is characterized in that the electrical heating component comprises a metal ceramic heating sheet 23, the metal ceramic heating sheet 23 is encapsulated in a metal protection shell composed of an upper sheet 24 and a lower sheet 25, a connection base 21 is connected onto the upper sheet 24, a PVC protection shell 20 is installed in the connection base 21, the PVC protection shell 20 and the connection base 21 are axially positioned through a threaded sleeve 19, an upper end of the threaded sleeve 19 is positioned on the PVC protection shell 20 through an annular boss 31 on the PVC protection shell 20, and a lower end thereof is rotationally installed on a threaded section 37 of the connection base 21; a power connector installation shell 18 is installed in the PVC protection shell 20, a temperature control switch 17 is installed in the power connector installation shell 18, a copper flat-core power input socket 15 is installed in the power connector installation shell 18, and a rotary upper cover 14 is installed on the power input socket 15; and an electric wire of the metal ceramic heating sheet 23 penetrates through the metal protection shell and the connection base 21 thereon, then penetrates through the PVC protection shell 20 to enter the power connector installation shell 18, then is electrically connected with the temperature control switch and a thermal fuse, and then is electrically connected with the power input socket 15, and a power plug 13 can be inserted into the power input socket 15 by rotating the rotary upper cover to expose the power input socket 15.

The upper sheet 24 and the lower sheet 25 are provided with annular grooves 35 for installing sealing pads 22, so as to implement a second waterproof and insulated sealing system for the metal ceramic heating sheet, a power wire and a wire lead point; and a thermal fuse 16 capable of directly sensing the temperature of the metal ceramic heating sheet 23 is installed on the upper sheet 24, the lower part of the PVC protection shell 20 and the upper sheet 24. The lower part of the connection base 21 is provided with a hollow structure for passage of liquid, so as to directly transfer, via the hollow structure, the temperature of the liquid to the temperature control switch 17 installed in the power connector installation shell 18 (heat is firstly transferred to a hollow bottom plate of the connection base 21, then to the PVC protection shell 20, then to the power connector installation shell 18 installed in a close fit manner, and finally to the temperature control switch 17).

A power input end of the metal ceramic heating sheet 23 is provided with an upper pressing sheet 11 and a lower pressing sheet 12, the upper pressing sheet 11 is installed in a groove of the upper sheet 24, the lower pressing sheet 12 is installed in a groove 36 of the lower sheet 25, a concave-convex buckle structure is provided on a joint surface of the upper pressing sheet and the lower pressing sheet, and the upper and lower sheets are jointed together by using an ultrasonic process, so as to implement a first waterproof and insulated sealing system for the power wire and the wire lead point; a wire sealing pad 27 is additionally disposed between the upper pressing sheet 11 and the metal ceramic heating sheet 23, a wire guide sleeve 28 for wire penetration is connected to the wire sealing pad 27, the wire guide sleeve 28 penetrates through the upper pressing sheet 11, the upper sheet 24 and the PVC protection shell 20 and is inserted into the power connector installation shell 18, a wire led out from the metal ceramic heating sheet 23 penetrates through the wire guide sleeve 28 to enter the power connector installation shell 18, and is electrically connected with the temperature control switch 17 and the thermal fuse 16 as well as the power input socket 15 in sequence, a hole for penetration of the wire guide sleeve in the upper pressing sheet is of a non-inverted cone structure and is inserted into a non-inverted cone hole in the upper sheet, the cone hole in the upper sheet is then inserted into a non-inverted cone hole in the PVC protection shell 20, a cone hole of the PVC protection shell 20 is then inserted into a non-inverted cone hole in the power connector installation shell 18, and when the wire guide sleeve 28 passes through each cone hole, multi-stage pressing seal is achieved, and it is ensured that liquid in the bag body cannot enter the power connector installation shell 18 along the wire.

The metal ceramic heating sheet 23 is wound with an insulating material 26 for insulation.

A bolt hole 29 is connected to the lower part of the threaded section of the connection base 21, one end of a bolt 30 is inserted into the bolt hole 29, and the other end is positioned in an insertion slot on the threaded sleeve 19 to prevent the threaded sleeve 19 from loosening during use.

The wire sealing pad 27 is a silicone pad, laterally having a hem for achieving lateral seal during pressing.

The second technical solution of the present invention is as follows.

A heatable fluid bag comprises a bag body 1, a liquid inlet 4 and a power access port being formed in the bag body 1, an extractable liquid inlet plunger 3 being installed in the liquid inlet 4, and the power access port 41 being electrically connected with an electrical heating component installed in the bag body 1. The heatable fluid bag is characterized in that the electrical heating component comprises a metal ceramic heating sheet 23, a wire end of the metal ceramic heating sheet 23 penetrates through a silicone sheet 6 to be located in a protection shell composed of an upper base 24' and a lower base 25', one ends of the upper base 24' and the lower base 25' together with the silicone sheet 6 form a sealed wire waterproof insulating sleeve, the other ends of the upper base 24' and the lower base 25' form a sealed or hollow protection sleeve, a thermal fuse 16 is attached to the ceramic heating sheet 23 and is covered with a fuse protection shell 19', and the fuse protection shell 19' is located in the protection sleeve; an upper pressing sheet 11 and a lower pressing sheet 12 are installed in a wire waterproof sleeve, the upper pressing sheet 11 and the lower pressing sheet 12 press the wire end of the ceramic heating sheet 23, a silicone sheet 8 is additionally disposed between the upper pressing sheet 11 and the ceramic heating sheet 23, the silicone sheet 8 is provided with a frustum-shaped insertion hole inserted into a through hole in the upper pressing sheet 11, two wires penetrate through the corresponding frustum-shaped insertion holes in the silicone sheet 8 respectively, are led out from the upper pressing sheet 11, and enter corresponding holes in a threading apparatus 10, the threading apparatus is inserted into a connection base 9 on a PVC insulation shell 20', the connection base 9 is fixed into the wire waterproof insulating sleeve, a temperature control switch 17 is installed in the PVC insulation shell 20', a power input socket 15 is also fixed into the PVC insulation shell 20', and a rotary upper cover 14 is installed on the power input socket 15; and a power plug 13 can be inserted into the power input socket 15 by rotating the rotary upper cover to expose the power input socket 15 with a square terminal.

The power plug 13 is a common plug or a clip-type plug 2 with a bulging bag power-off protection function.

The silicone sheet 8 is laterally provided with a waterproof hem.

An end, inserted into the wire waterproof insulating sleeve, of the connection base 9 is provided with two annular protrusions 7, the annular protrusions 7 being inserted into corresponding insertion slots in the wire waterproof insulating sleeve, so as to position the connection base in the wire waterproof insulating sleeve.

The present invention has the beneficial effects as follows. The present invention adopts multiple waterproof and insulating seals to form at least two independent insulating waterproof systems, and once one system is damaged, at least one system can play a protective role, thereby realizing separation of water and electricity, and completely meeting the requirements of international safety standards for electrical appliances.

The present invention adopts, but is not limited to, metal ceramics as a heating element, which has the advantages of small heating element size, high thermal efficiency, water proofing, insulation, safety, and long service life. Especially, a metal ceramic heating plate is encapsulated in metal, which is not only limited to a metal protection shell, so that not only the damage of a heating element can be effectively prevented, but also the waterproof effect and the heat transfer effect can be ensured.

The temperature fuse is used in the present invention to prevent a fire from occurring due to no liquid (water) burning.

The present invention adopts multiple waterproof and insulating seals to form at least two independent insulating waterproof systems, and once one system is damaged, at least one system can play a protective role, thereby realizing separation of water and electricity, and thoroughly preventing the occurrence of an electric leakage event. In particular, a wire has a silicone sleeve, and a conical threading hole is used to achieve waterproof insulation sealing of the wire.

The present invention adopts a square electrode pin, which enlarges a contact area between an external power supply and the pin, and can effectively prevent the failure caused by excessive current.

The electrical installation of the present invention adopts a double-layer protection (close fit between a PVC protection shell 20 and a power connector installation shell 18), which can ensure the normal operation in the case of one-layer damage, improve the safety, and prolong the service life.

DETAILED DESCRIPTION

The present invention will be further described below with reference to the drawings and embodiments.

Embodiment 1

Figure 1:
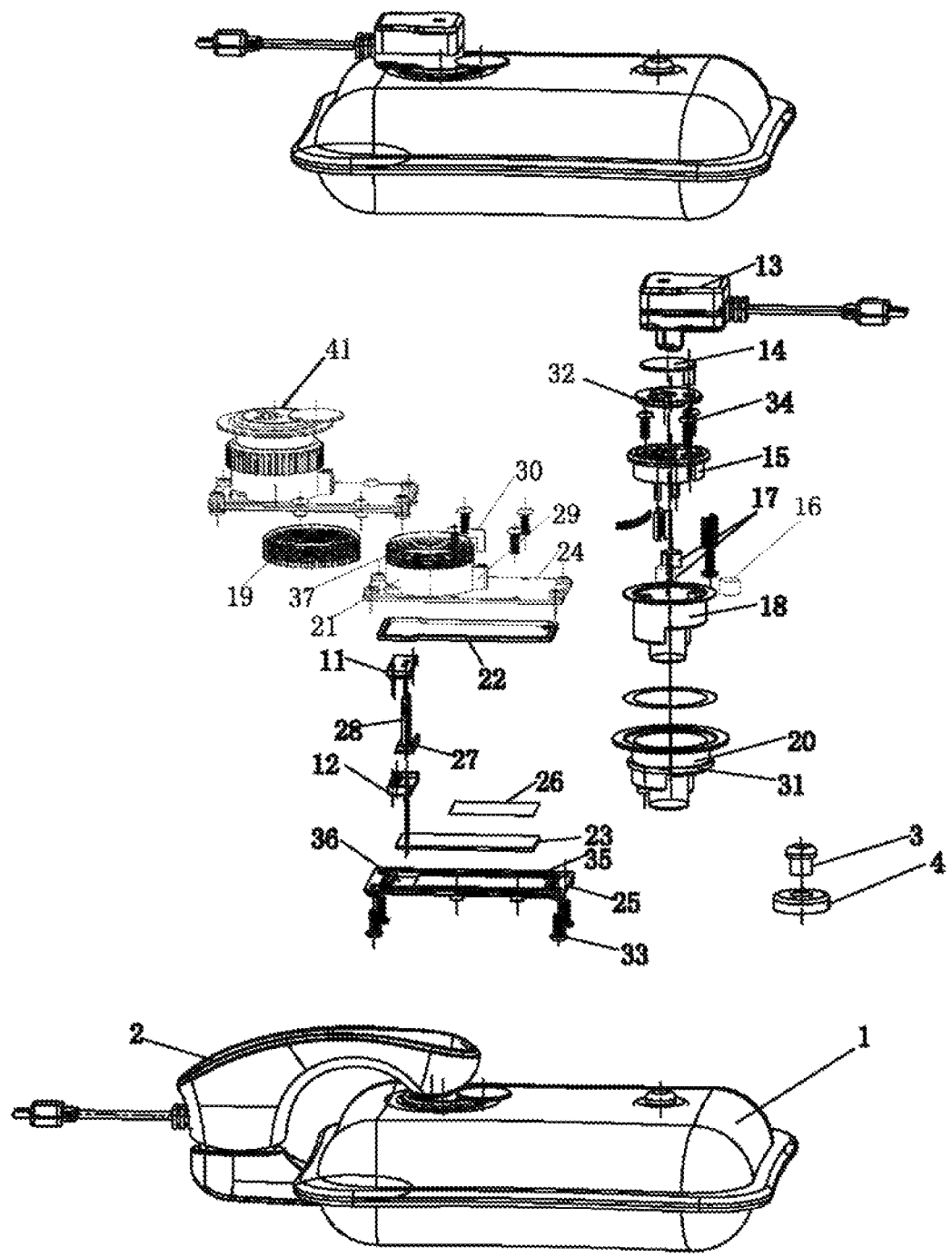
FIG. 1 is a first exploded structure diagram of the present invention.
Figure 3:
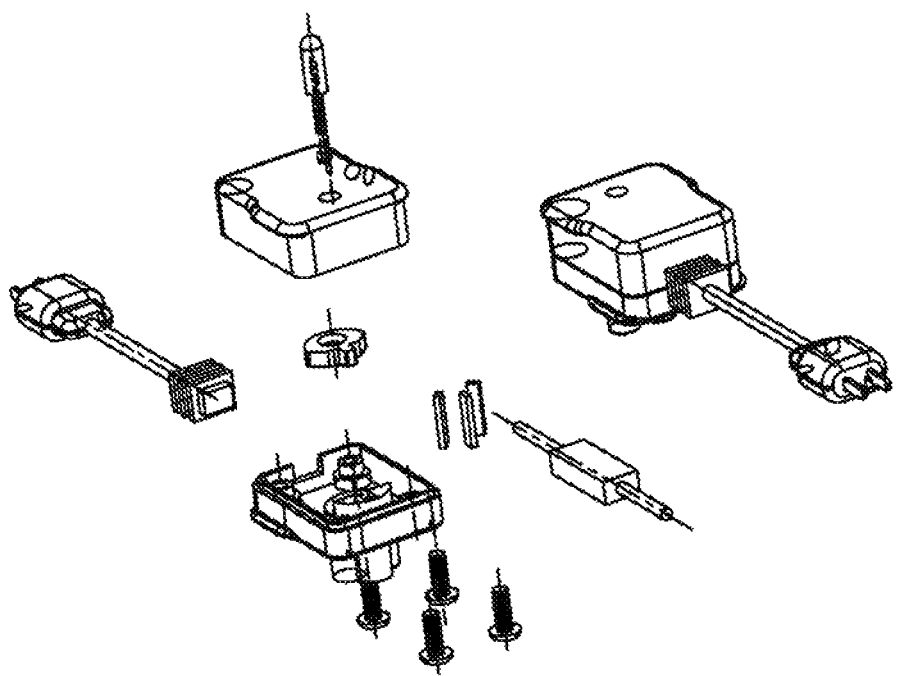
FIG. 3 is an exploded structure diagram of a power plug of the present invention.
Figure 4:
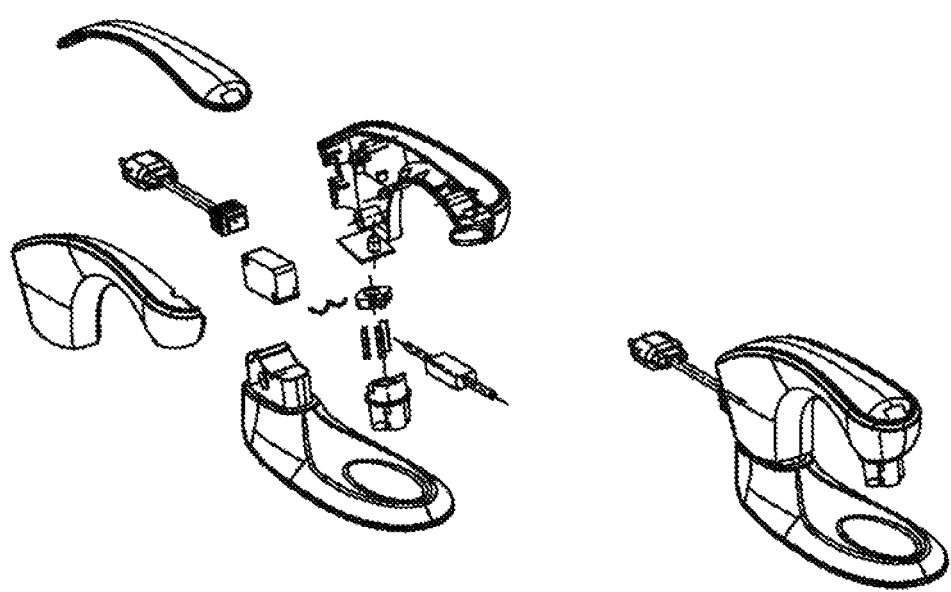
FIG. 4 is a structure diagram of a clip-type power plug of the present invention.
Figure 5:
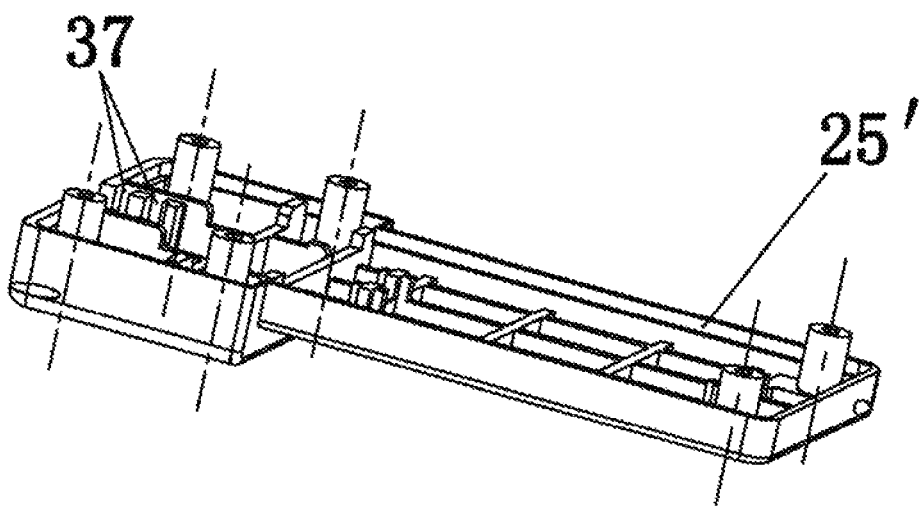
FIG. 5 is an enlarged structure diagram of a lower base 25' in FIG. 2.

As shown in FIG. 1, FIG. 3 and FIG. 4, a heatable fluid bag comprises a bag body 1, wherein a liquid inlet 4 and a power access port 41 are formed in the bag body 1, an extractable liquid inlet plunger 3 is installed in the liquid inlet 4, a waterproof connection between the power access port and the bag body 1 may be implemented by the prior art, and the power access port is electrically connected with an electrical heating component installed in the bag body 1; the electrical heating component comprises a metal ceramic heating sheet 23, the metal ceramic heating sheet 23 is encapsulated in a metal protection shell composed of an upper sheet 24 and a lower sheet 25, the upper sheet 24 and the lower sheet 25 may be fixedly connected through a screw 33, an annular groove 35 for adding an annular sealing pad 22 is formed in the lower sheet, and a matched annular convex slot is formed on the upper sheet; the metal ceramic heating sheet 23 is separated from liquid in the bag body 1 through the annular silicone sealing pad 22, and moreover, in order to secondarily insulate the metal ceramic heating sheet 23, it is necessary to wind a plurality of layers of insulating materials 26 before assembly; a power input end of the metal ceramic heating sheet 23 is provided with an upper pressing sheet 11 and a lower pressing sheet 12, the upper pressing sheet 11 is installed in a groove of the upper sheet 24, the lower pressing sheet 12 is installed in a groove 36 of the lower sheet 25, a concave-convex buckle structure is provided on a joint surface of the upper pressing sheet and the lower pressing sheet, and the upper and lower sheets are jointed together by using an ultrasonic process, so as to implement a waterproof and insulated sealing system for the metal ceramic heating sheet and a wire; and a wire sealing pad 27 with a hem (for preventing lateral leakage) is additionally disposed between the upper pressing sheet 11 and the metal ceramic heating sheet 23, a wire guide sleeve 28 for wire penetration is connected to the wire sealing pad 27, the wire guide sleeve 28 penetrates through the upper pressing sheet 11, the upper sheet 24 and a PVC protection shell 20 and is inserted into a power connector installation shell 18, a wire led out from the metal ceramic heating sheet 23 penetrates through the wire guide sleeve 28 to enter the power connector installation shell 18, and is electrically connected with a temperature control switch 17 (K301) and a thermal fuse 16 as well as a power input socket 15 in sequence, a hole for penetration of the wire guide sleeve in the upper pressing sheet is of a non-inverted cone structure and is inserted into a non-inverted cone hole in the upper sheet, the cone hole in the upper sheet is then inserted into a non-inverted cone hole in the PVC protection shell 20, a cone hole of the PVC protection shell 20 is then inserted into a non-inverted cone hole in the power connector installation shell 18, and when the wire guide sleeve 28 passes through each cone hole, multi-stage pressing seal is achieved, and it is ensured that the liquid in the bag body cannot enter the power connector installation shell 18 along the wire. A connection base 21 is connected to the upper sheet 24, the PVC protection shell 20 is installed in the connection base 21, the PVC protection shell 20 and the connection base 21 are axially positioned through a threaded sleeve 19, an upper end of the threaded sleeve 19 is positioned on the PVC protection shell 20 through an annular boss 31 on the PVC protection shell 20, and a lower end thereof is rotationally installed on a threaded section 37 of the connection base 21. The power connector installation shell 18 is installed in the PVC protection shell 20, and the PVC protection shell 20 and the power connector installation shell 18 are in close fit, so that when one of the protection shell 20 and the installation shell 18 is damaged, the other one can still normally work. One or two temperature control switches 17 are installed in the power connector installation shell 18, so that when one of the switches is damaged, the other one can still normally work. The temperature control switch 17 is attached to the lower part of the PVC protection shell 20 and above a hollow through groove, and can directly sense the temperature of water, and when the temperature of water reaches a set temperature, the temperature control switch is turned off to power off. The thermal fuse 16 is attached to a solid position of the upper sheet 24 and is located at the lower part of the PVC protection shell 20, so that the thermal fuse 16 directly senses the temperature of the metal ceramic heating sheet to prevent no water burning. In the case of no water burning, the temperature of the upper sheet covering the metal ceramic heating sheet 23 is rapidly increased, when the temperature exceeds a set temperature of the thermal fuse, it is necessary to immediately power off, and a product will be scrapped. The power input socket 15 is fixedly installed in the power connector installation shell 18, an upper cover 32 is installed on the power input socket 15 through a screw 34, and a rotary upper cover 14 is installed on the upper cover 32. An electric wire of the metal ceramic heating sheet 23 penetrates through the metal protection shell and the connection base 21 thereon, then penetrates through the PVC protection shell 20 to enter the power connector installation shell 18, then is electrically connected with the temperature control switch and the thermal fuse, and then is electrically connected with the power input socket 15. A power plug 13 can be inserted into the power input socket 15 by rotating the rotary upper cover to expose the power input socket 15. As shown in FIG. 1, the power plug 13 may be a common plug shown in FIG. 3 or a clip-type plug 2 with a bulging bag power-off protection function shown in FIG. 4.

During specific implementation, in order to prevent the threaded sleeve 19 from loosening during use, one or more bolt holes 29 may be connected to the lower part of a threaded section 37 of the connection base 21, one end of a bolt 30 is inserted into the bolt hole 29, and the other end is positioned in a horizontal or longitudinal insertion slot on the threaded sleeve 19 to prevent the threaded sleeve 19 from loosening during use.

Embodiment 2

Figure 2:
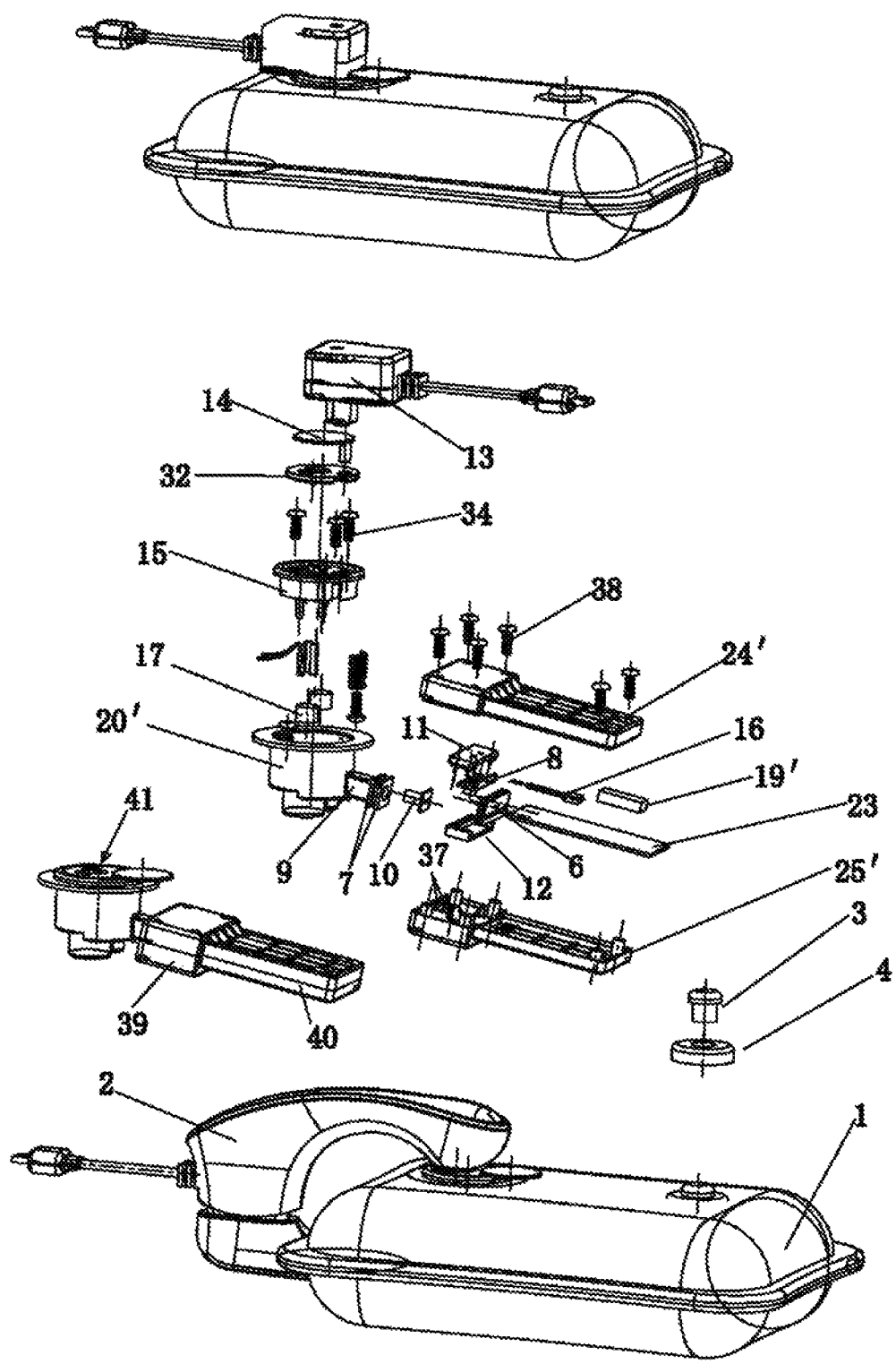
FIG. 2 is a second exploded structure diagram of the present invention.

As shown in FIG. 2, FIG. 3, FIG. 4, and FIG. 5, a heatable fluid bag comprises a bag body 1, wherein a liquid inlet 4 and a power access port are formed in the bag body 1, an extractable liquid inlet plunger 3 is installed in the liquid inlet 4, and the power access port is electrically connected with an electrical heating component installed in the bag body 1; the electrical heating component comprises a metal ceramic heating sheet 23, as shown in FIG. 2, a wire end of the metal ceramic heating sheet 23 penetrates through a silicone sheet 6 to be located in a protection shell (made of PVC material, metal material, or other materials) composed of an upper base 24' and a lower base 25', one ends of the upper base 24' and the lower base 25' together with the silicone sheet 6 form a sealed wire waterproof insulating sleeve, the other ends of the upper base 24' and the lower base 25' form a sealed or hollow protection sleeve 40 (being of a hollow structure in FIG. 2, with which the metal ceramic heating sheet is in direct contact with liquid in the bag body for rapid heating), a thermal fuse 16 is attached to the metal ceramic heating sheet 23 and is covered with a fuse protection shell 19', and the fuse protection shell 19' is located in the protection sleeve; an upper pressing sheet 11 and a lower pressing sheet 12 are installed in a wire waterproof sleeve, the upper pressing sheet 11 and the lower pressing sheet 12 press the wire end of the metal ceramic heating sheet 23, a silicone sheet 8 is additionally disposed between the upper pressing sheet 11 and the lower pressing sheet 12, the silicone sheet 8 is laterally provided with a hem for preventing lateral leakage, the front surface thereof is provided with two frustum-shaped insertion holes or frustum-shaped wire guide sleeves for wire penetration, the frustum-shaped insertion holes are inserted into conical through holes (non-inverted) in the upper pressing sheet 11, two wires penetrate through the corresponding frustum-shaped insertion holes or frustum-shaped wire guide sleeves in/on the silicone sheet 8 respectively, are led out from the upper pressing sheet 11, and enter corresponding holes in a threading apparatus 10, and the threading apparatus is inserted into a connection base 9 on a PVC insulation shell 20'; and an end, inserted into the wire waterproof insulating sleeve, of the connection base 9 is provided with two annular protrusions 7, the annular protrusions 7 being inserted into corresponding insertion slots in the wire waterproof sleeve, so as to position the connection base in the wire waterproof insulating sleeve. A temperature control switch 17 is installed in the PVC insulation shell 20', a power input socket 15 is also fixed in the PVC insulation shell 20', an upper cover 32 is installed on the power input socket 15 through a screw 34, and a rotary upper cover 14 is installed on the upper cover 32; and a power plug 13 shown in FIG. 3 or a clip-type power plug 2 shown in FIG. 4 can be inserted into the power input socket 15 by rotating the rotary upper cover 14 to expose the power input socket 15 with a square terminal.

In addition, in order to adapt to the development needs of the Internet technology, hot water bags in Embodiment 1 and Embodiment 2 may be electrically transformed during the specific implementation, and a communication board is installed in the power connector installation shell 18 for installing the temperature control switch and the thermal fuse additionally, thereby achieving remote control over a mobile phone, monitoring a heating state in real time through an APP, and switching on or off a power supply remotely.

Further, the metal ceramic heating sheet in Embodiment 1 and Embodiment 2 of the present invention may be rectangular, square, circular, diamond, or of other shapes. The metal ceramic heating sheet may also be replaced with other similarly shaped heating elements. The metal ceramic heating sheet of the present invention may also be replaced with heating elements having other non-sheet structures or made of other materials even under appropriate and non-creative improvement.

Further, the heatable fluid bag of the present invention may also be started directly in a frozen state without malfunctioning, and may also be put in a refrigerator for refrigeration to be used as an ice bag.

Parts not involved in the present invention such as electrical schematic diagrams are the same as those in the prior art or may be implemented by using the prior art, and may also be implemented by referring to Chinese Patent 2013800424341 (or PCT/NZ2013/000162).

The invention claimed is:

1. A heatable fluid bag, comprising a bag body, a liquid inlet and a power access port being formed in the bag body, an extractable liquid inlet plunger being installed in the liquid inlet, and the power access port being electrically connected with an electrical heating component installed in the bag body, wherein the electrical heating component comprises a metal ceramic heating sheet, the metal ceramic heating sheet is encapsulated in a metal protection shell composed of an upper sheet and a lower sheet, a connection base is connected onto the upper sheet, a PVC protection shell is installed in the connection base, the PVC protection shell and the connection base are axially positioned through a threaded sleeve, an upper end of the threaded sleeve is positioned on the PVC protection shell through an annular boss on the PVC protection shell, and a lower end thereof is rotationally installed on a threaded section of the connection base; a power connector installation shell is installed in the PVC protection shell, a temperature control switch is installed in the power connector installation shell, a copper flat-core power input socket is installed in the power connector installation shell, and a rotary upper cover is installed on the power input socket; and a wire of the metal ceramic heating sheet penetrates through the metal protection shell and the connection base thereon, then penetrates through the PVC protection shell to enter the power connector installation shell, then is electrically connected with the temperature control switch and a thermal fuse, and then is electrically connected with the power input socket, and a power plug can be inserted into the power input socket by rotating the rotary upper cover to expose the power input socket.

2. The heatable fluid bag according to claim 1, wherein the upper sheet and the lower sheet are provided with annular grooves for installing sealing pads, so as to implement a second waterproof and insulated sealing system for the metal ceramic heating sheet, a power wire and a wire lead point; a thermal fuse capable of directly sensing the temperature of the metal ceramic heating sheet is installed on the upper sheet, the lower part of the PVC protection shell and the upper sheet; and the lower part of the connection base is provided with a hollow structure for passage of liquid, so as to directly transfer, via the hollow structure, the temperature of the liquid to the temperature control switch installed in the power connector installation shell.

3. The heatable fluid bag according to claim 1, wherein a power input end of the metal ceramic heating sheet is provided with an upper pressing sheet and a lower pressing sheet, the upper pressing sheet is installed in a groove of the upper sheet, the lower pressing sheet is installed in a groove of the lower sheet, a concave-convex buckle structure is provided on a joint surface of the upper pressing sheet and the lower pressing sheet, and the upper and lower sheets are jointed together by using an ultrasonic process, so as to implement a first waterproof and insulated sealing system for the power wire and the wire lead point; a wire sealing pad is additionally disposed between the upper pressing sheet and the lower pressing sheet, a wire guide sleeve for wire penetration is connected to the wire sealing pad, the wire guide sleeve penetrates through the upper pressing sheet, the upper sheet and the PVC protection shell and is inserted into the power connector installation shell, a wire led out from the metal ceramic heating sheet penetrates through the wire guide sleeve to enter the power connector installation shell, and is electrically connected with the temperature control switch and the thermal fuse as well as the power input socket in sequence, a hole for penetration of the wire guide sleeve in the upper pressing sheet is of a non-inverted cone structure and is inserted into a non-inverted cone hole in the upper sheet, the cone hole in the upper sheet is then inserted into a non-inverted cone hole in the PVC protection shell, a cone hole of the PVC protection shell is then inserted into a non-inverted cone hole in the power connector installation shell, and when the wire guide sleeve passes through each cone hole, multi-stage pressing seal is achieved, and it is ensured that liquid in the bag body cannot enter the power connector installation shell along the wire.

4. The heatable fluid bag according to claim 3, wherein the metal ceramic heating sheet is wound with an insulating material for insulation.

5. The heatable fluid bag according to claim 1, wherein a bolt hole is connected to the lower part of the threaded section of the connection base, one end of a bolt is inserted into the bolt hole, and the other end is positioned in an insertion slot on the threaded sleeve to prevent the threaded sleeve from loosening during use.

6. The heatable fluid bag according to claim 3, wherein the wire sealing pad is a silicone pad, laterally having a hem for achieving lateral seal during pressing.

7. The heatable fluid bag according to claim 1, wherein the power plug is a common plug or a clip-type plug with a bulging bag power-off protection function.

8. A heatable fluid bag, comprising a bag body, a liquid inlet and a power access port being formed in the bag body, an extractable liquid inlet plunger being installed in the liquid inlet, and the power access port being electrically connected with an electrical heating component installed in the bag body, wherein the electrical heating component comprises a metal ceramic heating sheet, a wire end of the metal ceramic heating sheet penetrates through a silicone sheet to be located in a protection shell composed of an upper base and a lower base, one ends of the upper base and the lower base together with the silicone sheet form a sealed wire waterproof insulating sleeve, the other ends of the upper base and the lower base form a sealed or hollow protection sleeve, a thermal fuse is attached to the metal ceramic heating sheet and is covered with a fuse protection shell, and the fuse protection shell is located in the protection sleeve; an upper pressing sheet and a lower pressing sheet are installed in the wire waterproof insulating sleeve, the upper pressing sheet and the lower pressing sheet press the wire end of the metal ceramic heating sheet, a silicone sheet is additionally disposed between the upper pressing sheet and the lower pressing sheet, the silicone sheet is provided with a frustum-shaped insertion hole inserted into a through hole in the upper pressing sheet, two wires penetrate through the corresponding frustum-shaped insertion holes in the silicone sheet respectively, are led out from the upper pressing sheet, and enter corresponding holes in a threading apparatus, the threading apparatus is inserted into a connection base on a PVC insulation shell, the connection base is fixed into the wire waterproof insulating sleeve, a temperature control switch is installed in the PVC insulation shell, a power input socket is also fixed into the PVC insulation shell, and a rotary upper cover is installed on the power input socket; and a power plug can be inserted into the power input socket by rotating the rotary upper cover to expose the power input socket with a square terminal.

9. The heatable fluid bag according to claim 8, wherein the silicone sheet is laterally provided with a waterproof hem.

10. The heatable fluid bag according to claim 8, wherein an end, inserted into the wire waterproof insulating sleeve, of the connection base is provided with two annular protrusions, the annular protrusions being inserted into corresponding insertion slots in the wire waterproof insulating sleeve, so as to position the connection base in the wire waterproof insulating sleeve.

11. The heatable fluid bag according to claim 8, wherein the power plug is a common plug or a clip-type plug with a bulging bag power-off protection function.

\* \* \* \* \*